United States Patent [19]

Miwa et al.

[11] 4,438,199

[45] Mar. 20, 1984

[54] MEASURING COMPOSITION

[75] Inventors: Naoto Miwa, Ibaragi; Hiroshi Nakajima, Uji, both of Japan

[73] Assignees: Mitsubishi Petrochemical Co., Ltd., Tokyo; Unitika Ltd., Amagasaki, both of Japan

[21] Appl. No.: 267,245

[22] Filed: May 26, 1981

[30] Foreign Application Priority Data

May 26, 1980 [JP] Japan .................................. 55-69880

[51] Int. Cl.$^3$ ......................... C12N 9/04; C12N 9/10; C12Q 1/32; C12Q 1/48
[52] U.S. Cl. .................................... 435/190; 435/14; 435/15; 435/17; 435/26; 435/194; 435/810; 435/822; 435/828; 435/832; 435/876
[58] Field of Search .................... 435/4, 14, 17, 15, 21, 435/26, 810, 194, 190, 832, 822, 876, 828

[56] References Cited

U.S. PATENT DOCUMENTS 3,509,025  4/1970  Bergmeyer et al. .................. 435/14

OTHER PUBLICATIONS

Kamel et al., Chemical Abstracts, 66:52894b, 4980, (1967).
Bergmeyer, *Methods of Enzymatic Analysis*, Academic Press, New York, 1196–1201, (1974).
Barman, *Enzyme Handbook*, vol. 1, 379, 380, 73, 74, (1969).

*Primary Examiner*—Esther M. Kepplinger
*Attorney, Agent, or Firm*—Oblon, Fisher, Spivak, McClelland & Maier

[57] ABSTRACT

An analytical composition comprises glucokinase and glucose-6-phosphate dehydrogenase.

3 Claims, 3 Drawing Figures

MEASURING COMPOSITION

BACKGROUND OF THE INVENTION

1. Field of the Invention

This invention relates to a composition for measuring intravital ingredients such as glucose, ATP, creatine kinase, other phosphotransferases, various glucose-releasing glycosidases, and the like.

2. Description of the Prior Art

In clinical testing for the measurement of glucose or creatine kinase (hereinafter abbreviated CPK), the usual analytical method employed comprises a coupling enzyme system of hexokinase (hereinafter abbreviated as HK) and glucose-6-phosphate dehydrogenase (hereinafter abbreviated G6PDH). This system is referred to as the HK/G6PDH system, and has been extensively used because of the high availability of HK.

The principle of the system can be illustrated by the following reaction scheme:

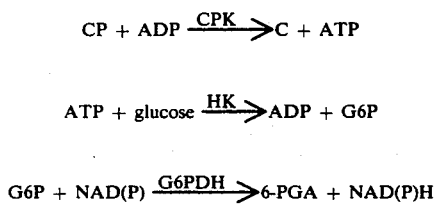

In the above reaction sequence, CP represents creatine phosphate, C represents creatine, ADP represents adenosine 5'-diphosphate, ATP represents adenosine 5'-triphosphate, G6P represents glucose-6-phosphate, NAD(P) represents nicotinamidoadeninedinucleotide (phosphate), NAD(P)H represents reduced nicotinamidoadeninedinucleotide (phosphate), and 6-PGA represents 6-phosphogluconic acid. The enzymes which catalyze reactions (1), (2) and (3) are CPK, HK, and G6PDH, respectively.

HK, however, has the drawback that it literally acts on many hexose and phosphorylate sugars other than glucose, such as fructose and mannose, which exist in the intravital liquids. HK of yeast origin which is commonly used in the KH/G6PDH system shows a 1.8 times higher reaction rate for fructose than for glucose. Each of these phosphorylated hexoses is finally converted to G6P by the action of phosphomannose isomerase (hereinafter abbreviated as PMI) or phosphoglucose isomerase (hereinafter abbreviated as PGI) which are also present within intravital liquids by the scheme shown below which results in a positive error of the measured value.

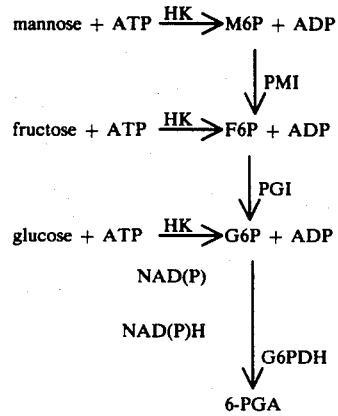

In the above scheme, M6P represents mannose-6-phosphate, and F6P represents fructose-6-phosphate.

As a result of an intensive study whose objective has been to eliminate the drawbacks of the HK/G6PDH system, it has been discovered that glucokinase (hereinafter abbreviated as GK) has a high substrate specificity for glucose as a phosphotransferase and thus can act as a substitute for HK. This discovery is the basis of the present invention.

SUMMARY OF THE INVENTION

An object of the present invention is to provide a coupling enzyme system of high specificity for glucose.

Briefly, this object and other objects of the present invention as hereinafter will become more readily apparent can be attained by an analytical enzyme containing composition comprising glucokinase and glucose-6-phosphate dehydrogenase.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
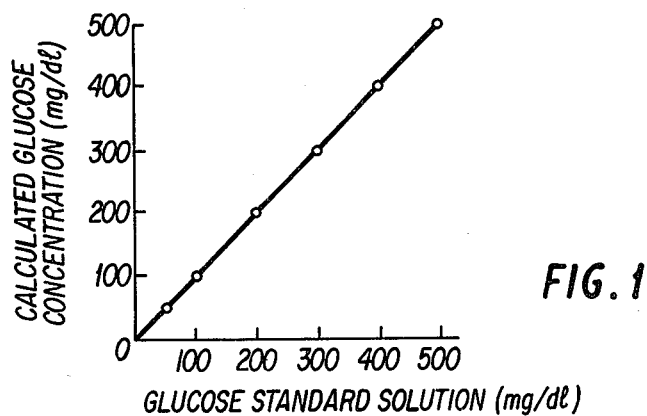
FIG. 1 is a graph of the results obtained for measuring standard glucose containing samples by the composition of Example 1.

HK and GK are distinctly differentiated from each other by the International Biochemical Union (IBU), Enzyme Committee (EC), and are completely different enzymes. The enzyme number for HK is EC 2.7.1.1., and that for GK is EC 2.7.1.2. (for example, see Enzyme Handbook vol. 1, pp. 377–380, compiled by T. E. Barman and published by Springer-Verlag CO. (1969)).

The GK/G6PDH system of the present invention, wherein GK is combined with G6PDH, has such a high specificity for glucose in comparison to the conventional HK containing system, that the presence of such sugars as fructose or mannose in samples has almost no influence on the results obtained. In addition, the GK/G6PDH system of the present invention is usable for measuring ATP, various phosphotransferases, and glucose-releasing glycosidases as well as CPK which is an important diagnostic item in clinical tests.

The GK component of the present invention can be obtained from any suitable source of animal origin or from *Aerobacter aerogenes*. However, thermostable GK obtained from thermophilic bacteria, e.g., *Thermus thermophilus, Bacillus stearothermophilus*, or the like, is preferred because of its excellent stability and preservability.

The G6PDH component of the present composition can be derived from any suitable source also, however, the preferred G6PDH is one which acts not only on NADP, but also on NAD. Suitable G6PDH sources include mesophilic bacteria, such as *Leuconostoc mesenteroides, Pseudomonas fluorescens*, and the like. Thermostable G6PDH obtainable from thermophilic bacteria (e.g., *Thermus thermophilus, Bacillus stearothermophilus,* and the like) capable of acting on both NAD and NADP and excellent in stability and preservability is also desired.

In preparing the GK and G6PDH components, known techniques may properly be combined for extraction, purification, and the like, of the enzymes.

The essential components of the present composition are GK and G6PDH, and other ingredients may be compounded therewith in order to prepare an analytical composition which can measure such intravital ingredients as glucose, CPK, ATP, and the like. Suitable additional components of the composition include, for example, a substrate for phosphotransferase to be measured (phosphoric acid donor), a substrate for glycosidase to be measured, ADP or a salt thereof, ATP or a salt thereof, glucose, NAD or NADP or a salt thereof, a magnesium-containing salt, a buffer solution, and the like. In addition, thiol compounds, chelating reagents, inhibitors for specific reactions, antiseptics, surfactants, stabilizers, and the like may also be utilized, if necessary.

The concentrations of the essential components in the present composition range from 0.1 to 20 u/ml for GK and 1 to 20 u/ml for G6DH. Additional ingredients may properly be compounded in the present invention in amounts determined by the materials to be measured. However, the following concentrations are provided as a general guide for the preparation of suitable compositions.

| | |
|---|---|
| Substrate of phosphotransferase (phosphate donor) to be measured | 0 to 40 mM |
| Substrate for glycosidase to be measured | 0 to 40 mM |
| ADP or salt thereof | 0 to 20 mM |
| ATP or salt thereof | 0 to 20 mM |
| Glucose | 0 to 40 mM |
| NAD, NADP or salt thereof | 0.1 to 10 mM |
| Magnesium-containing salt | 1 to 10 mM |
| Buffer solution (pH 5 to 10) | 10 to 500 mM |

The composition of the present invention may be prepared by compounding or mixing the above-described ingredients in an arbitrary order. With the composition of the invention, extremely accurate analyses can be performed with no errors having been experienced with the GK/G6PDH system.

The composition of the present invention finds utility in the measurement of such clinically important materials as glucose, CPK, ATP, and the like as described hereinabove and, in addition, it is effectively applicable to the measurement of the activity of glucose-releasing glycosidase, thus finding wide-spread use in biochemical research and food analysis.

Having generally described the invention, a further understanding can be obtained by reference to certain specific examples which are provided herein for purposes of illustration only and are not intended to be limiting unless otherwise specified.

EXAMPLE 1

30 $\mu$ of GK extracted and purified from cells of *Thermus thermophilus* (ATCC 27634, FERM-P 2988) in a conventional manner and 20 u of G6PDH obtained from *Leuconostoc mesenteroides* were dissolved in 10 ml of a 100 mM tris-hydrochloric acid buffer solution (pH 7.5) containing 1.5 mM NADP, 5 mM magnesium acetate, and 1.4 mM ATP, thereby preparing a composition within the scope of the present invention.

The thus prepared composition was maintained at 37° C., and 0.6 ml of the composition was placed in a cuvette having a light-path length of 1 cm. The absorbance was measured at 340 nm (Ao) in a spectrophotometer having a cell chamber similarly thermostated at 37° C. Thereafter, 4 $\mu$l of a standard glucose sample was placed in the cuvette, and the enzymatic reaction was allowed to proceed. After 5 minutes, the reaction plateau was reached and the absorbance of the solution was measured at 340 nm (A). This procedure was repeated for a number of glucose samples of different concentrations. The glucose concentration in each sample was calculated according to the following equation:

$$\text{Glucose Concentration (mg/dl)} = \frac{A - Ao}{6.22} \times \frac{\text{Amount of final reaction solution (604 } \mu\text{l)}}{\text{Sample amount (4 } \mu\text{l)}} \times \frac{\text{Molecular weight of glucose (180)}}{10} = 437 \times (A - Ao)$$

The results obtained are shown in FIG. 1. As is clear from FIG. 1, good linearity and high accuracy were obtained.

EXAMPLE 2

The procedure of Example 1 was used except that 1.5 mM of NAD was used instead of NADP in order to prepare a composition within the scope of the present invention.

Glucose in standard samples was determined in the same manner as described in Example 1 using the aboveprepared composition. As a result, the same good linearity and high accuracy results as obtained in Example 1 were also obtained.

EXAMPLE 3

40 u of GK and 40 u of G6PDH used in Example 1 were dissolved in 10 ml of a 100 mM imidazole-acetic acid buffer solution (pH 6.5) containing 20 mM creatinephosphoric acid, 1 mM ADP, 12 mM glucose, 1.6 mM NAD, 5 mM magnesium acetate, 4 mM AMP, and 40 mM dithiothreitol.

CPK in a standard serum, "Multi-Enzyme Control C", made by Hyland, Div. Travenol Laboratories, Inc., Costa Mesa, Calif. and CPK in a diluted solution thereof were measured at 37° C. in a conventional manner using the above-prepared composition and a commercially available CPK-measuring kit, "CPK n−1", made by Worthington Biochemical Corp., Freehold, N.J. By this means, a correlation between the two composition was made.

Figure 2:
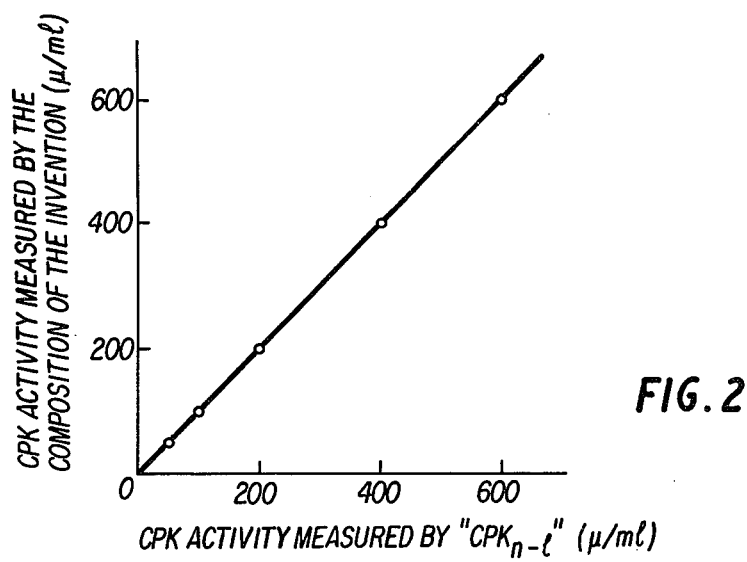
FIG. 2 is a graph showing the results of an examining correlation between the composition of Example 1 of the present invention and a commercially available CPK measuring kit using a standard serum.

The results obtained are shown in FIG. 2, and a good correlation was obtained.

EXAMPLE 4

The procedure of Example 3 was used except that 1.5 mM of NADP was used instead of NAD in order to prepare a compositon within the scope of the present invention.

The correlation with a commercially available CPK-measuring kit was examined in the same manner as described in Example 3 using the above-prepared composition. A good correlation was obtained.

EXAMPLE 5

42 u of GK extracted and purified from cells of *Bacillus stearothermophilus* (NCA 1503) in a conventional manner and 26 u of G6PDH were dissolved in 10 ml of a 100 mM tris-hydrochloric acid buffer solution (pH 8.6) containing 1.8 mM NAD, 5 mM magnesium phosphate, and 1.3 mM ATP.

Figure 3:
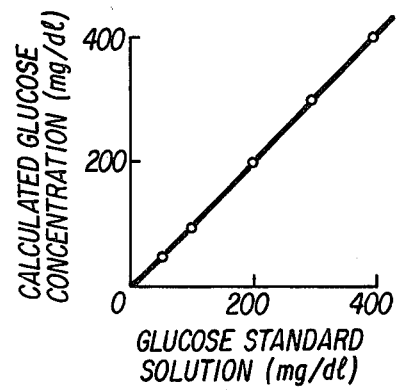
FIG. 3 is a graph of the results obtained for measuring standard glucose containing samples by the composition of Example 5.

Glucose in standard samples of different glucose concentrations was determined in the same manner as described in Example 1 using the above-prepared composition. As is clear from FIG. 3, good linearity and high accuracy were obtained.

EXAMPLE 6

The procedure of Example 5 was used except that 1.5 mM of NADP was used instead of NAD.

Glucose in standard samples of different glucose concentrations was determined in the same manner as described in Example 1 using the above-prepared composition. As a result, the same good linearity and high accuracy which were obtained in Example 5 were also obtained.

Having now fully described this invention, it will be more apparent to one of ordinary skill in the art that many changes and modifications can be made thereto without departing from the spirit or scope of the invention, as set forth herein.

What is claimed as new and desired to be secured by Letters Patent of the United States is:

1. An analytical composition, consisting of:
   from 0.1 to 20 $\mu$/ml glucokinase and from 1 to 20 $\mu$/ml glucose-6-phosphate dehydrogenase either one or both of said enzymes being thermostable and being obtained by extraction of a species of thermophilic bacteria.

2. The analytical composition of claim 1, wherein said glucokinase is obtained from thermophilic bacteria selected from the group consisting of *Thermus thermophilis* and *Bacillus stearothermophilus*.

3. The analytical composition of claim 1, wherein said glucose-6-phosphate dehydrogenase is obtained from thermophilic bacteria selected from the group consisting of *Thermus thermophilis* and *Bacillus stearothermophilus*.

* * * * *